US00PP19896P2

(12) United States Plant Patent
Dark

(10) Patent No.: US PP19,896 P2
(45) Date of Patent: Apr. 7, 2009

(54) ***GARDENIA* PLANT NAMED 'CROWN JEWEL'**

(50) Latin Name: *Gardenia augusta*
Varietal Denomination: Crown Jewel

(76) Inventor: Philip Dark, 9985 US 64 W, Siler City, NC (US) 27344

( * ) Notice: Subject to any disclaimer, the term of this patent is extended or adjusted under 35 U.S.C. 154(b) by 0 days.

(21) Appl. No.: 12/069,406

(22) Filed: Feb. 11, 2008

(51) Int. Cl.
*A01H 5/00* (2006.01)

(52) U.S. Cl. ..... Plt./255

(58) Field of Classification Search ..... Plt./255
See application file for complete search history.

*Primary Examiner*—S. B McCormick Ewoldt

(57) ABSTRACT

A new cultivar of *GARDENIA* named 'CROWN JEWEL' that is characterized by cold hardiness, a dwarf spreading habit, double fragrant blooms, and a soft texture. In combination these traits set 'CROWN JEWEL' apart from all other existing varieties of *GARDENIA* known to the inventor.

2 Drawing Sheets

Genus: *GARDENIA*.
Species: *augusta*.
Denomination: 'CROWN JEWEL'.

BACKGROUND OF THE INVENTION

The present invention relates to a new and distinct cultivar of *GARDENIA* that is grown as an ornamental evergreen flowering shrub. The new cultivar is known botanically as *GARDENIA augusta* and will be referred to hereinafter by the cultivar name 'CROWN JEWEL'.

The new *Gardenia* variety named 'CROWN JEWEL' is the product of a formal breeding program established by the inventor in 1998 at the inventor's nursery in Siler City, N.C. The purpose of the breeding program was to obtain cold-hardy, double blooming cultivars.

'CROWN JEWEL' is a seedling selection arising from the inventor's controlled cross-pollination of the *Gardenia augusta* 'Kleim's Hardy' (unpatented) and *Gardenia augusta* 'Chuck Hayes' (U.S. Plant Pat. No. 8,755). The inventor harvested pollen from the anthers of 'Kleim's Hardy' with a cotton swab and deposited it on the stigma of 'Chuck Hayes'. The seeds were harvested in spring 1999 and transplanted to one gallon containers in summer 1999. 'CROWN JEWEL' was selected in June 2000 based on double bloom and horizontal habit.

In comparison with each of its parent varieties) 'CROWN JEWEL' differs as follows. Whereas 'CROWN JEWEL' is compact and spreading in habit, 'Kleim's Hardy' is an upright variety whose height after two years is approximately 60 cm which is 50% taller than 'CROWN JEWEL'. In addition, the flowers of 'CROWN JEWEL' are double in form whereas the flowers of 'Kleim's Hardy' are single. In comparison with 'Chuck Hayes') 'CROWN JEWEL' is more densely branched and bears more flowers. Whereas a 2 year old plant of 'Chuck Hayes' typically bears 50–75 flowers, a similarly aged plant of 'CROWN JEWEL' bears more than 100 flowers. The flowers of both 'Chuck Hayes' and 'CROWN JEWEL' are double.

Whilst the parent varieties are the closest varieties of *Gardenia* known to the inventor within the market class of evergreen flowering shrubs, other varieties of *Gardenia* have been developed for the greenhouse or indoor potted, floral market. These varieties of *Gardenia*, which include *Gardenia* 'Kimberley' (U.S. Plant Pat. No. 15,189) are typically described as having cold tolerance down to 3 degrees Celsius whereas 'CROWN JEWEL' and its parents exhibit cold tolerance of −15 degrees Celsius, or USDA Hardiness Zone 7.

The first asexual reproduction of 'CROWN JEWEL' was conducted by the inventor in 2000. The method used for asexual propagation was rooting of stem cuttings using perlite and misting. The characteristics of 'CROWN JEWEL' have been determined stable during successive generations of asexual reproductions.

SUMMARY OF THE INVENTION

The following traits have been repeatedly observed and represent the characteristics of the new *GARDENIA* cultivar 'CROWN JEWEL'. These traits in combination distinguish 'CROWN JEWEL' from all other varieties known to the inventor. 'CROWN JEWEL' has not been tested under all possible conditions and phenotypic differences may be observed with variations in environmental, climatic and cultural conditions, without however, any difference in genotype.

1. 'CROWN JEWEL' is spreading to prostrate in habit reaching only 60 cm in 4 years.
2. 'CROWN JEWEL' has medium to small sized leaves for the species.
3. The flowers of 'CROWN JEWEL' bloom profusely and possess an intense sweet scent.
4. 'CROWN JEWEL' is hardy to USDA 7.

BRIEF DESCRIPTION OF THE DRAWINGS

The accompanying two color drawings illustrate the overall appearance of the new cultivar 'CROWN JEWEL' showing the colors as true as it is reasonably possible to obtain in colored reproductions of this type. Colors in the photographs may differ from the color values cited in the detailed botanical description, which accurately describe the actual colors of the new variety of *GARDENIA* named 'CROWN JEWEL'.

The drawing labeled as FIG. 1 illustrates a 2 year old plant of 'CROWN JEWEL' growing out of doors in Siler City, N.C.

Figure 1:
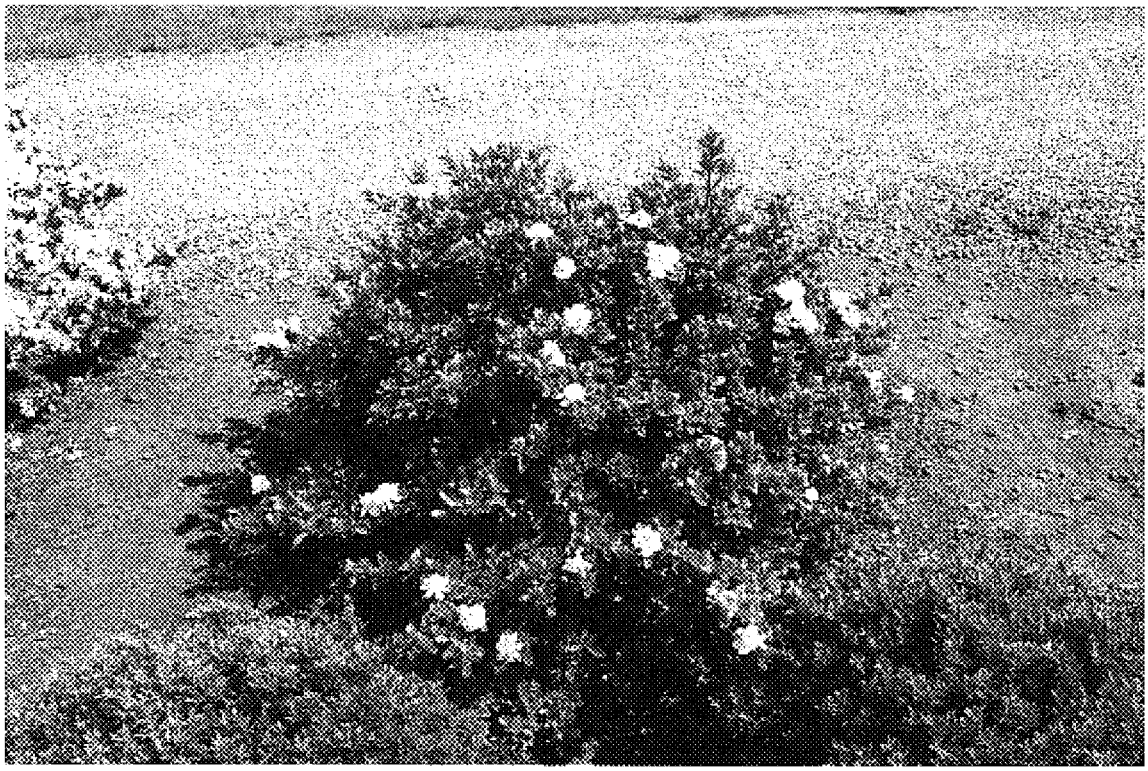
Figure 2:
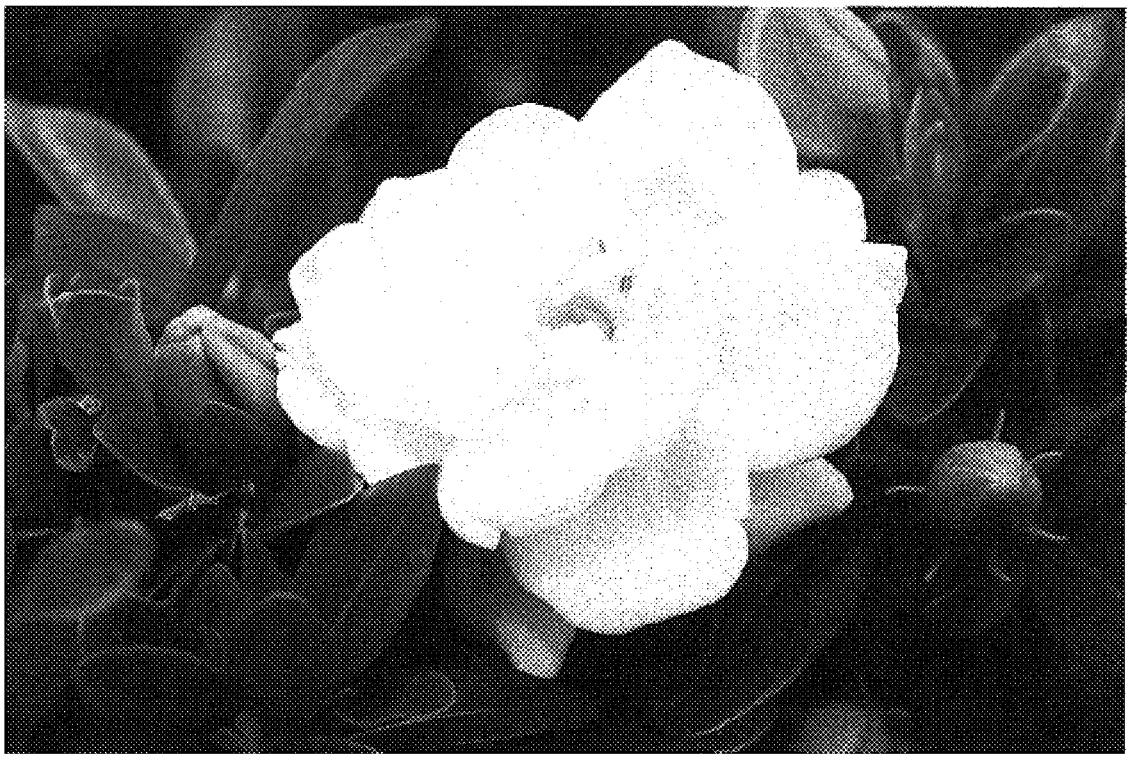

The drawing labeled as FIG. 2 illustrates a close-up view of a single flower of 'CROWN JEWEL'.

All drawings were made using conventional techniques and although colors may appear different from actual colors due to light reflectance they are as accurate as possible by conventional photography.

BOTANICAL DESCRIPTION OF THE PLANT

The following is a detailed description of 'CROWN JEWEL' as grown out of doors in 3 gallon containers growing in pine bark substrate. Data was collected in 2007 from plants approximately 2 years old. The color determinations are in accordance with the 2001 Royal Horticultural Society Colour Chart of the Royal Horticultural Society, London, England, except where general color terms of ordinary dictionary significance are used. The growing requirements are similar to the species.

Family: *Rubiaceae.*
Botanical classification: *GARDENIA augusta.*
Genus: *GARDENIA.*
Species: *augusta.*
Variety Denomination: 'CROWN JEWEL'.
Common name: Common *gardenia* or Cape Jessamine.
Use: Evergreen flowering shrub for the landscape.
Container size: 3 gallon or 5 gallon.
Cultural requirements: Full sun to partial shade. Requires little to no pruning. Prefers acidic, well-drained, moist soil.
Parentage:
- *GARDENIA augusta.*—'Kleim's Hardy' (Male parent).
- *GARDENIA augusta.*—'Chuck Hayes' (Female parent).

Bloom period: Early June.
Plant habit: Compact, dense, upright.
Vigor: Less vigorous (slower growing) than most *Gardenias*.
Dimensions: 46 cm in height and 61 cm in width.
Hardiness USDA Zone 7.
Root system: Fibrous.
Propagation: Stem cuttings.
Time to develop roots 2 to 4 weeks.
Crop time from planting a one year old liner.—2 to 3 months to 1 gallon; 4 to 5 months to 3 gallon; 12 months to 5 gallon.
Disease and pest susceptibility: Typical of the species.
Branching Habit: Very densely branched.
Stem:
- *Shape.*—Terete.
- *Color* (*over one year old*).—197A.
- *Color* (*current season*).—138B.
- *Width* (*one year old stems*).—3 mm to 4 mm.
- *Length* (*main stems*).—17 cm to 21 cm.
- *Length* (*secondary stems*).—20 mm to 30 mm.
- *Internode length.*—10 mm to 20 mm.
- *Surface.*—Pubescent with short, scattered but dense tomentum.
- *Description of hairs.*—Short; tan-grey-white in color.

Foliage:
- *Leaf arrangement.*—Opposite and decussate; occasionally whorled in threes.
- *Stipules present or absent.*—Present.
- *Stipule appearance.*—Membranous sheath around stem above point of attachment of leaves.
- *Stipule shape.*—Broadly elliptic with acute to retuse apex; 2 stipules fused into one sheath-like structure.
- *Stipule attachment.*—Sheathing, connate.
- *Stipule color.*—Translucent, N144A.
- *Stipule dimensions.*—6 mm in length and 4 mm in width.
- *Leaves.*—Division: Simple. Shape: Elliptic. Length: 28 mm to 50 mm (the larger end of this range from leaves occurring on non-flowering shoots). Width: 13 mm to 20 mm (the larger end of the range from leaves occurring on non-flowering shoots). Apex: Bluntly acute. Base: Broadly cuneate. Venation pattern: Pinnate. Vein color (adaxial surface): N144A. Vein color (abaxial surface): 145C. Margin type: Entire. Leaf surface (adaxial): Glabrous with thick, waxy cuticle layer. Leaf surface (abaxial): Essentially glabrous. Young leaf color (adaxial surface): 137A. Young leaf color (abaxial surface): 138B. Mature leaf color (adaxial surface): 137B. Mature leaf color (abaxial surface): 138B. Leaf attachment: Short petiolate. Petiole dimensions: 2 mm to 3 mm in length and 1 mm to 2 mm in diameter. Petiole surface: Very short pubescent. Petiole hairs: Translucent, very short hairs. Petiole color: 144B.

Inflorescence:
- *Inflorescence form.*—Solitary.
- *Quantity of flowers per inflorescence.*—One.
- *Quantity of inflorescences per plant.*—Over 100 on a two year old plant.
- *Time and duration of flowering.*—Early June for three to four weeks.
- *Flowers.*—Aspect: Salverform. Diameter including calyx, corolla, petals: 55 mm to 70 mm. Height or depth of flower: 40 mm to 60 mm. Bud: Shape: Tubular, flaring and bulging at apical upper third. Color: 144B. Surface: Glabrous, but numerously pitted. Description of surface structures: None, waxy cuticle only. Dimensions: 35 mm to 50 mm in length and 12 mm to 15 mm in diameter.
- *Peduncle.*—Dimension: 3 mm to 5 mm in length and 3 mm to 4 mm in width. Shape: Terete. Color: 143C. Surface: With scattered pubescence. Description of hairs: Translucent, very short.
- *Calyx.*—Shape: Narrowly elliptic to linear, fused on the basal half with adjacent sepals, not fused above; ridged through with rib-like projections; rib-like projections free (unfused) for apical 15 mm to 18 mm. Dimensions: 20 mm to 25 mm in length and 12 mm in diameter. Color (inner and outer surface): 143C. Surface (outer): Waxy, subglabrous; with very few short translucent hairs. Surface (inner): Glabrous.
- *Sepals.*—Present or absent: Present; persistent and accrescent as fruit develops. Number: Six. Fused or unfused: Fused, but only along basal half. Color (adaxial surface): 143C. Color (abaxial surface): 145D. Surface (adaxial): Waxy, subglabrous; with very few short translucent hairs. Surface (abaxial): Glabrous.
- *Corolla.*—Shape of tube: Salverform. Dimensions of tube: 20 mm to 25 mm in length and 10 mm in width. Surface of tube: Outer surface glabrous; inner surface bearing long, white, ciliate hairs. Tube color: 145A. Number of lobes: Six. Shape of lobes: Obovate with rounded to subtruncate apices. Lobe color: White (adaxial); Striped 145A and 145C abaxially.

*Petals.*—Petals fused or unfused: Fused, but only along basal half. Shape of lobes: Obovate, undulate-revolute on margins, adjacent petals overlapping each other for ⅓ to ⅔ of length. Flower single or double: Double — formal style. Number of petals and petaloids: Six true petals and 18 petaloids. Color of petals and petaloids (adaxial surface): White, aging to 12D after 1 to 2 days. Color of petals and petaloids (abaxial surface): White, aging to 12A and 12C after 1 to 2 days. Surface (both): Glabrous. Length of petaloids: 15 mm to 30 mm (sizes progressively smaller toward center of unfurling flower). Width of petaloids: 12 mm to 24 mm (sizes progressively smaller toward center of unfurling flower). Arrangement/opening sequence of petals and petaloids: All 6 petals expand outward to a flattened (open-faced flower) position (almost reflexed); inner 18 petaloids are oriented upright, but slightly incurved, all 18 petaloids spreading slightly (but never becoming reflexed) as flower opens.

Reproductive organs:

*Number of stamens.*—6, but sometimes rudimentary.

*Stamens fused or unfused at base.*—Not fused to other stamens, but fused in middle of petal at point where corolla lobe transitions into corolla tube.

*Staman dimensions.*—10 mm in length and 1 mm in width.

*Stamen color.*—161A.

*Anther shape.*—Linear.

*Anther dimensions.*—10 mm in length, 1 mm in width.

*Anther color.*—161A.

*Pollen color.*—Light yellow.

*Pollen amount.*—Minimal.

*Pistil number.*—1, partially splitting into 3 to 5.

*Pistil shape.*—Cylindrical, but flaring at apical third.

*Pistil length.*—20 mm.

*Pistil width.*—3 mm for the style to 6 mm for the stigma.

*Pistil color.*—White for the style, 145D for the stigma.

*Pistil surface.*—Pubescent.

*Stigma shape.*—Cylindrical, somewhat balloon-like, developing shallow longitudinal valleys via partial splitting along multiple lines as stigma ages.

*Stigma dimensions.*—10 mm in length and 3 mm to 5 mm in width.

*Style color.*—145D.

*Style shape.*—Linear and flat (in cross-section).

*Style dimensions.*—5 mm to 8 mm in length and 1 mm to 2 mm in width.

*Style color.*—White.

*Ovary position.*—Inferior.

*Ovary shape.*—Elliptoid.

*Ovary dimensions.*—5 mm to 6 mm in length, 3 mm at the style to 6 mm at the stigma in width.

*Ovary color.*—145D.

Seed: None observed.

What is claimed is:

1. A new and distinct cultivar of *GARDENIA* plant named 'CROWN JEWEL' as described and illustrated herein.

* * * * *